(12) United States Patent
White

(10) Patent No.: US 9,549,724 B2
(45) Date of Patent: Jan. 24, 2017

(54) ADAPTOR FOR SURGICAL RETRACTOR BLADES

(75) Inventor: William R. White, Parker, CO (US)

(73) Assignee: NSI-US, Inc., Peachtree City, GA (US)

(*) Notice: Subject to any disclaimer, the term of this patent is extended or adjusted under 35 U.S.C. 154(b) by 87 days.

(21) Appl. No.: 13/612,255

(22) Filed: Sep. 12, 2012

(65) Prior Publication Data

US 2013/0066163 A1 Mar. 14, 2013

Related U.S. Application Data

(60) Provisional application No. 61/534,139, filed on Sep. 13, 2011.

(51) Int. Cl.
*A61B 1/32* (2006.01)
*A61B 17/04* (2006.01)
*A61B 17/02* (2006.01)

(52) U.S. Cl.
CPC .......... *A61B 17/0401* (2013.01); *A61B 17/02* (2013.01)

(58) Field of Classification Search
CPC .. A61B 17/64–17/6491; A61B 17/02–17/0293
USPC ............... 600/201–235; 606/53–59
See application file for complete search history.

(56) References Cited

U.S. PATENT DOCUMENTS

| | | | |
|---|---|---|---|
| 5,616,117 A | 4/1997 | Dinkler et al. | |
| 5,893,831 A | 4/1999 | Koros et al. | |
| 5,984,865 A | 11/1999 | Farley et al. | |
| 6,042,540 A * | 3/2000 | Johnston et al. | 600/213 |
| 6,042,542 A | 3/2000 | Koros et al. | |
| 6,228,083 B1 * | 5/2001 | Lands | A61B 18/1445 606/207 |
| 6,305,868 B1 * | 10/2001 | Kinoshita et al. | 403/49 |
| 6,733,444 B2 | 5/2004 | Phillips | |
| 6,898,829 B2 * | 5/2005 | Loe et al. | 24/599.5 |
| 7,569,014 B2 * | 8/2009 | Bass | A61B 17/02 294/82.1 |
| 7,588,537 B2 * | 9/2009 | Bass | 600/234 |
| 7,938,829 B2 * | 5/2011 | Mullaney | 606/59 |
| 8,038,611 B2 | 10/2011 | Raymond et al. | |
| 8,361,073 B2 * | 1/2013 | Mullaney | 606/59 |
| 2001/0009971 A1 * | 7/2001 | Sherts et al. | 600/231 |
| 2002/0115911 A1 * | 8/2002 | Knight et al. | 600/228 |
| 2010/0217089 A1 | 8/2010 | Farley et al. | |

* cited by examiner

*Primary Examiner* — Jan Christopher Merene
*Assistant Examiner* — Steven Cotroneo
(74) *Attorney, Agent, or Firm* — Dorr, Carson & Birney, PC

(57) ABSTRACT

An adaptor for removably engaging surgical retractor blades to a retractor frame has a recess with a latch mechanism at its proximal end for removably securing the adaptor to the rail of a retractor frame, and a spring-loaded locking jaw mechanism at its distal end for removably engaging a retractor blade.

8 Claims, 4 Drawing Sheets

ADAPTOR FOR SURGICAL RETRACTOR BLADES

RELATED APPLICATION

The present application is based on and claims priority to the Applicant's U.S. Provisional Patent Application 61/534,139, entitled "Adaptor For Surgical Retractor Blades," filed on Sep. 13, 2011.

BACKGROUND OF THE INVENTION

Field of the Invention

The present invention relates generally to the field of surgical retractors. More specifically, the present invention discloses an adaptor for removably engaging a surgical retractor blade to a retractor frame.

Statement of the Problem

Current surgical retractor systems utilize a retractor frame with two rails running generally parallel to the surgical incision line. Typically, there is one rail on each of the lateral sides of the incision. These retractor frames incorporate a mechanism to attach a set of retractor blades to these rails at intervals along their length to retract the patient's tissue along the surgical incision.

Existing retractor frames used for surgery on the lumbar spine include an integrated locking mechanism to hold each retractor blade onto the retractor frame. This is done by utilizing an adaptor. These systems present multiple issues with the clinical retraction of tissue for typical lumbar spine surgical procedures, as well as adding additional steps, time, and manual manipulation time to the process. This in turn can lead to longer times in the operating room, longer times under anesthesia, as well as related retraction issues that can lead to increased difficulty of the surgeon to gain access to the proper tissue for these specific types of procedures.

Many conventional retractor systems employ a blade adaptor in which the surgeon must first connect the retractor blade to the adaptor, then attach a handle to this assembly, and then attach this assembly to the frame rail, and finally remove the handle. This process is dependent on precise alignment of the assembly of the blade, adaptor and handle with respect to the retractor frame. Only then can this assembly be attached to the retractor frame in the third step, above. This process adds time to the procedure, and in many cases, the anatomical alignment is incorrect when connecting the assembly of the blade, adaptor and handle to the retractor frame. This can lead to failure of tissue retraction, or misalignment of the blade with respect to the specific surgical anatomy that the surgeon is attempting to retract. This may require the surgeon to completely remove the system and start over, which in turn leads to additional operating room time, expense, and potential patient safety concerns. Such locking mechanisms add a degree of manual manipulation that the surgeon must be concerned with during the procedure.

Solution to the Problem

To address these shortcomings in the prior art, the present invention provides a blade adaptor that incorporates integrated self-locking mechanisms allowing the surgeon to quickly and easily attach the adaptor to the frame rail and the retractor blade to the adaptor. In particular, the present blade adaptor includes a C-shaped recess and latch mechanism at its proximal end to initially attach the adaptor by simply dropping the proximal end of the blade adaptor onto the retractor frame rail. The latch mechanism prevents the adaptor from dislodging from the retractor frame rail. Second, the surgeon attaches the post of a retractor blade to a handle. The surgeon then retracts the appropriate tissue with the handle/blade assembly, and then simply retracts the handle/blade, and aligns this assembly with the blade adaptor attached to the retractor frame. The surgeon clicks the post of the retractor blade into the spring-loaded locking jaw at the distal end of the blade adaptor to lock the blade post into the jaw of the blade adaptor. Finally, the surgeon releases the handle from the blade post to complete the assembly.

This blade adaptor offers the surgeon a simple and quick method to precisely place retractor blades into the correct anatomical position, and helps to eliminate blade misalignment. This direct means of attachment provides additional benefits to the surgeon and the patient, namely; this system provides the surgeon with a simple and quick means to retract specific tissue and helps to eliminate misalignment of the retractor blades. This system also provides a quick means to apply multiple blades without the need to reposition the initial blades that have been set in place. Finally, it allows the surgeon to visualize and securely retract specific tissue without additional manipulation, and re-alignment. The present blade adaptor provides a unique and quick means to apply retraction to specific tissue, and thus reduces operating room time and related expense.

SUMMARY OF THE INVENTION

This invention provides an adaptor for surgical retractor blades having a recess with a latch mechanism at its proximal end for removably securing the adaptor to the rail of a retractor frame, and a spring-loaded locking jaw mechanism at its distal end for engaging a retractor blade.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
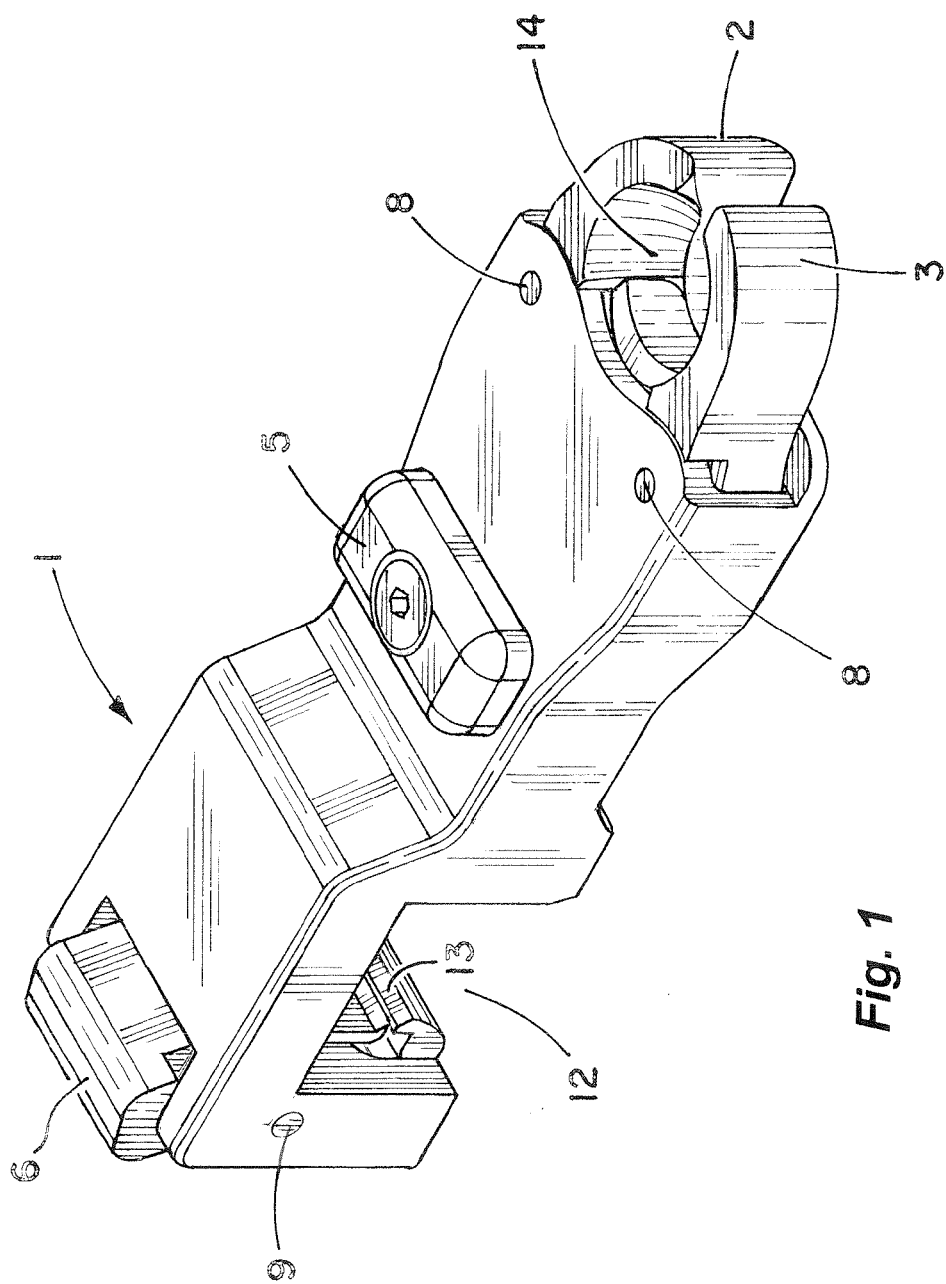
FIG. 1 is a perspective view of an embodiment of the present adaptor 1.
Figure 2A:
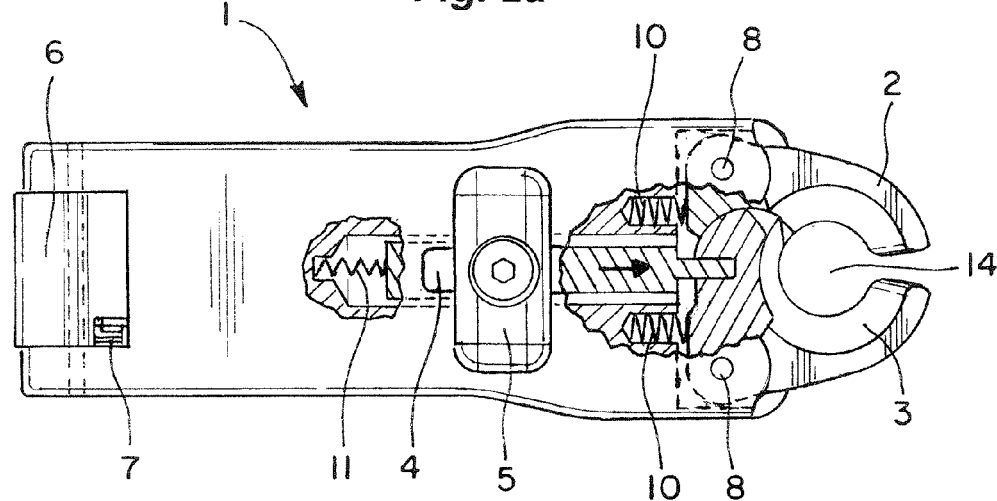
FIG. 2a is a top view of the adaptor 1 showing the jaws 2, 3 in the closed position, with portions of the inner mechanism shown in cross-section.
Figure 2B:
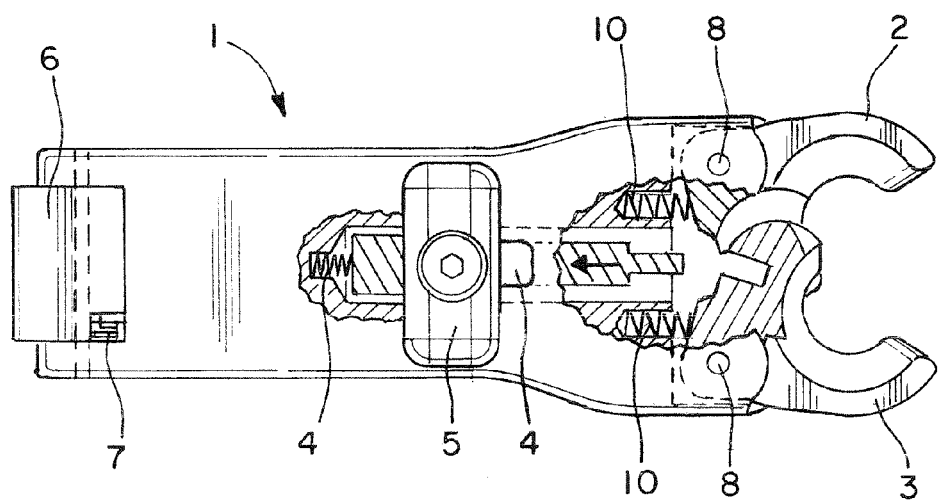
FIG. 2b is a top view of the adaptor 1 showing the jaws 2, 3 in the open position, with portions of the inner mechanisms shown in cross-section.
Figure 3:
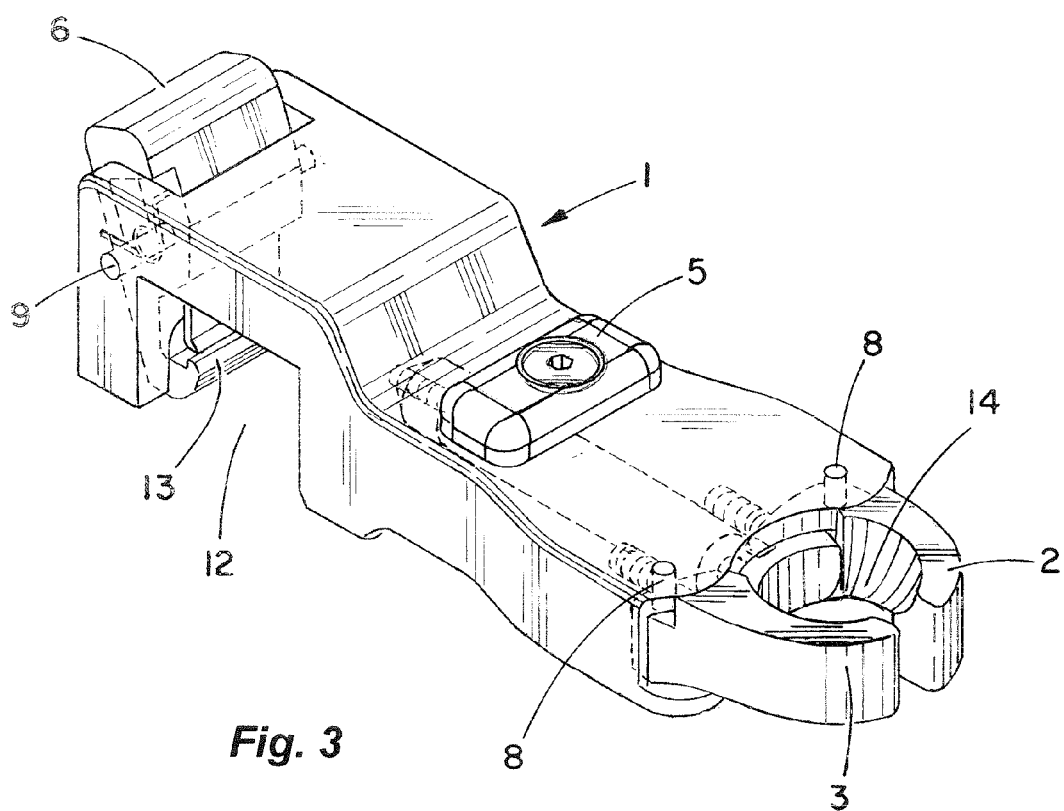
FIG. 3 is a perspective view of the adaptor 1 with portions of the inner mechanism shown in hidden lines.

Turning to FIG. 1, a perspective view is shown of an embodiment of the present adaptor 1. FIGS. 2a and 2b are corresponding top views with portions of the latch mechanism and jaw mechanism shown in cross-section. Similarly, FIG. 3 is a perspective view with portions of these mechanisms shown in hidden lines.

Figure 4:
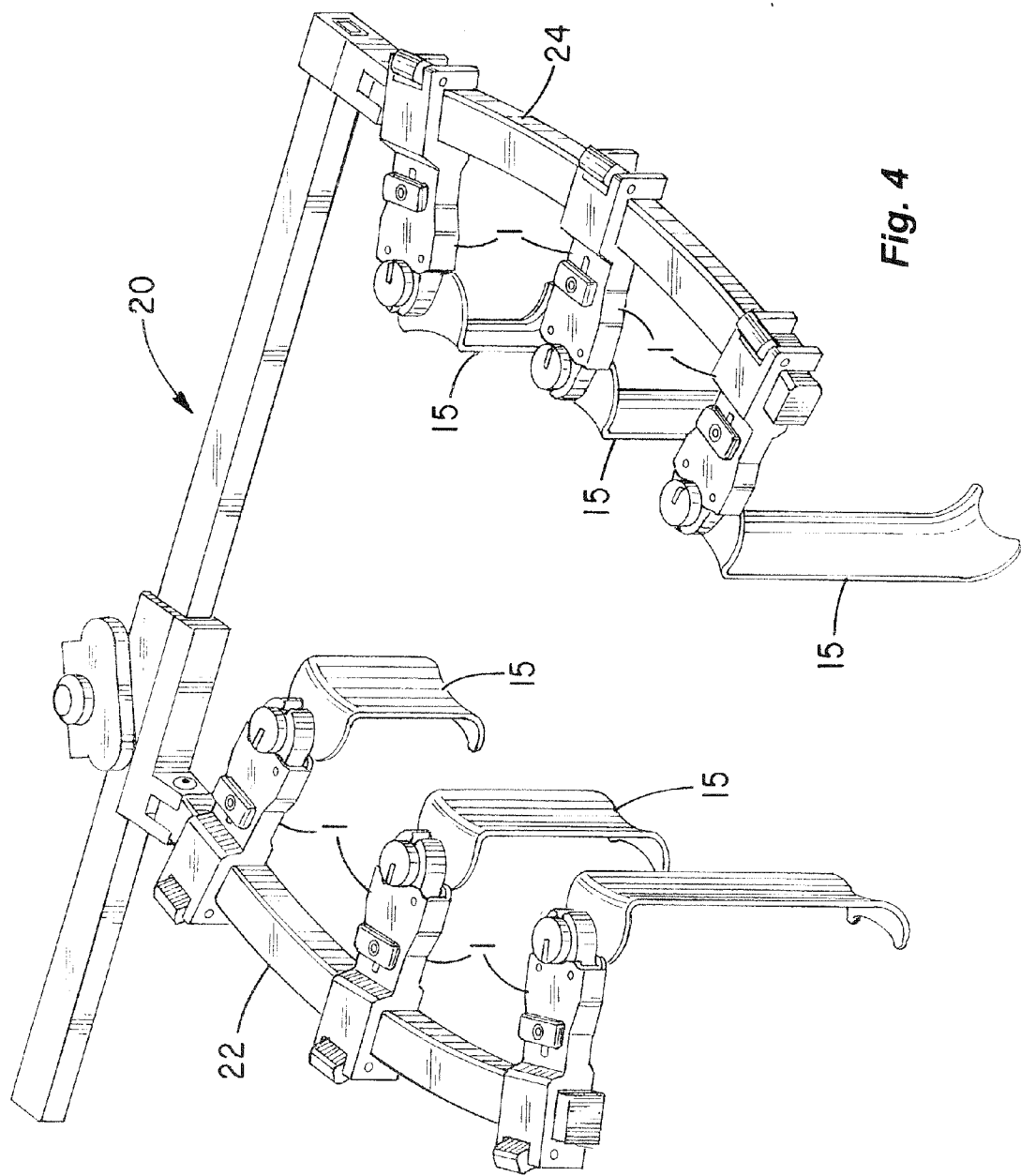
FIG. 4 is a perspective view of the surgical retractor frame 20 with a set of adaptors 1 and retractor blades 15 attached to the rails 22, 24 of a retractor frame 20.

The adaptor 1 has an elongated member with a C-shaped recess 12 adjacent to its proximal end. This recess 12 has a cross-sectional profile that allows the adaptor 1 to be dropped over one of the rails 22, 24 of the retractor frame, as illustrated in FIG. 4. A latch 6 is pivotably mounted on pins 9 and biased by a spring 7 to removably engage and secure the proximal end of the body of the adaptor 1 to the rail 22, 24. The adaptor 1 can be removed by manually releasing the latch 6 and then lifting the adaptor 1 from the rail 22, 24. In the embodiment shown in the accompanying drawings, the latch 6 includes a pivoting member that is pivotably mounted to the proximal end of the adaptor 1 with a lower portion extending into the recess 12. A lip 13 on the lower portion of the pivoting member protrudes into the recess 12 to engage and retain the rail 22, 24 in the recess 12.

A spring-loaded jaw mechanism extends from the distal end of the elongated member of the adaptor 1 to grip the post of a retractor blade 15. The jaw mechanism includes two opposing jaws 2 and 3 that are pivotably mounted on pins 8 at the distal end of the adaptor to pivot between open and closed positions. In the closed position, the jaws 2, 3 define a rounded socket 14 for holding the post of a retractor blade 15, as shown in FIG. 4. The jaws 2, 3 are biased to the open position by two springs 10, as shown in FIG. 2b.

A sliding rod 4 housed within the adaptor 1 behind the jaws 2, 3 can be manually actuated by means of a handle 5 extending through a slot in the elongated member of the adaptor 1. In the preferred embodiment of the present invention, this handle 5 is used to slide the distal tip of the sliding rod 4 between a retracted position as shown in FIG. 2b, and an extended position shown in FIG. 2a. In the retracted position, the distal tip of the sliding rod 4 is withdrawn from contact with the base portions of the jaws 2, 3, thereby allowing the springs 10 to pivot the jaws 2, 3 to their open position in FIG. 2b. In the extended position, the distal tip of the sliding rod 4 advances into a slot defined between the base portions of the jaws 2, 3, as shown in FIG. 2a. Insertion of the distal tip of the sliding rod 4 between the base portions of the jaws 2, 3 prevents rotation of the jaws 2, 3, and thereby locks the jaws 2, 3 in their closed position shown in FIG. 2a. A spring 11 attached to the proximal end of the sliding rod 4 biases the rod 4 forward so that its distal tip locks the jaws 2, 3 in the closed position by default.

To operate the present device, the surgeon first manually retracts the rod 4 by sliding the handle 5 rearward as shown in FIG. 2b. This withdraws the distal tip of the rod 4 from its locking position between the base portions of the jaws 2, 3 and allows the biasing springs 10 to pivot the jaws 2, 3 to the open position to receive the post of a retractor blade 15.

After the jaws 2, 3 are in the open position depicted in FIG. 2b, the post of a retractor blade 15 can be inserted into the socket 14 defined by open jaws 2, 3. The post of the retractor blade 15 contacts the base portions of the jaws 2, 3 upon its insertion into the socket 14. The force exerted by the retractor blade 15 overcomes the biasing forces exerted by the springs 10, and thereby moves the jaws 2, 3 to the closed position around the post of the retractor blade 15 as shown in FIG. 4.

The surgeon can then release the handle 5. This allows the spring 11 to push the sliding rod 4 forward until its distal tip slides into the slot between the base portions of the jaw 2, 3 to lock the jaws 2, 3 in the closed position with the post of the retractor blade engaged in the socket 14. It should be noted that other types of actuators could be substituted to manually operate the sliding rod 4, and thereby move the jaws 2, 3 between the open and closed positions.

FIG. 4 is a perspective view of a surgical retractor frame 20 with a set of adaptors 1 and retractor blades 15 attached to the rails 22, 24 of a retractor frame 20. The retractor frame 20 serves as the structural support for the remaining components. The retractor frame 20 is an elongated metal member with a generally rectangular cross-sectional shape. The rails 22 and 24 also have a generally rectangular cross-sectional shape. The proximal end of one of the rails 22 carries a slider mechanism that allows this rail 22 to slide along the retractor frame 20. The proximal end of the other rail 24 is rigidly attached to the end of the retractor frame 20. This enables the spacing between the rails 22, 24 to be adjusted by sliding the movable rail 22 along the retractor frame 20 to a desired position, and then actuating the ratchet of the slider mechanism to engage the teeth on the retractor frame 20, thereby fixing the position of the movable rail 22.

A series of retractor blades 15 can be removably attached along the rails 22, 24 by a surgeon as depicted in FIG. 4. Typically, retractor blades 15 are attached to both retractor rails 22, 24 at intervals around the surgical site. Each retractor blade 15 can be attached to a rail 22, 24 using the sequence of steps mentioned above. First, the C-shaped recess 12 at the proximal end of the adaptor 1 is placed over the rail 22, 24 at the desired location. The spring-loaded latch 6 prevents the adaptor 1 from dislodging from the retractor frame rail 22, 24. Next, the surgeon attaches the post of a retractor blade 15 to a handle. The surgeon then retracts the appropriate tissue with the handle/blade assembly, retracts the handle/blade assembly, and aligns this assembly with the adaptor 1 attached to the retractor frame rail 22, 24. The surgeon clicks the post of the retractor blade 15 into the spring-loaded jaws 2, 3 at the distal end of the adaptor 1 to lock the blade post into the jaws 2, 3 of the blade adaptor 1. Finally, the surgeon releases the handle from the post of the retractor blade 15 to complete the assembly.

After the surgical procedure has been completed, each retractor blade 15 can be removed from the assembly by sliding the handle 5 rearward to open the jaws 2, 3 and release the post of the retractor blade 15. Alternatively, the adaptor 1 and retractor blade 15 can be removed together from the retractor frame rail 22, 24 by releasing the spring-loaded latch 6 at the proximal end of the adaptor 1.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. An adaptor for removably securing a surgical retractor blade having a post to a retractor frame having a rail, said adaptor comprising:

an elongated member with a proximal end and a distal end; a recess in the proximal end to receive the rail of the retractor frame; a latch for removably securing the rail of the retractor frame in the recess; and a jaw mechanism extending from the distal end for removably securing the post of the retractor blade to the adaptor, said jaw mechanism having:

(a) two opposing jaws having base portions, said jaws being respectively spring-biased to an open position and pivoting about the base portions in opposite directions with respect to one another to define a socket for removably engaging the post of the retractor blade in a closed position; and (b) a slot defined between the base portions of the jaws;

a sliding rod sliding within the elongated member having a distal tip sliding into the slot between the base portions of the jaws when the sliding rod is extended toward the socket, to thereby lock the jaws in the closed position around the post of the retractor blade, and wherein the distal tip retracts from the slot when the sliding rod is retracted to allow the jaw to be spring-biased to the open position; and a handle connected to and extending from the sliding rod through the elongated member for manual operation of the sliding rod.

2. The adaptor of claim 1 further comprising a spring biasing the sliding rod in an extended position to lock the jaws in the closed position.

3. The adaptor of claim 1 wherein the jaws are pivotably mounted to the distal end of the elongated member and pivot between the open and closed positions.

4. The adaptor of claim 1 wherein the latch comprises:

a pivoting member pivotably mounted to the proximal end of the adaptor with a lower portion extending into the recess; and a lip on the lower portion of the pivoting member protruding into the recess to engage and retain the rail of the retractor frame in the recess.

5. An adaptor for removably securing a surgical retractor blade having a post to a retractor frame having a rail, said adaptor comprising:

an elongated member with a proximal end and a distal end;

a recess in the proximal end to receive the rail of the retractor frame;

a latch for removably securing the rail of the retractor frame in the recess, said latch having:

(a) a pivoting member pivotably mounted to the proximal end of the adaptor with a lower portion extending into the recess; and (b) a lip on the lower portion of the pivoting member protruding into the recess to engage and retain the rail of the retractor frame in the recess;

a jaw mechanism extending from the distal end for removably securing the post of the retractor blade to the adaptor, said jaw mechanism having:

(a) two opposing jaws having base portions, both pivotably mounted to the distal end defining a socket for removably engaging the post of the retractor blade, with both jaws pivoting about the base portions in opposite directions with respect to one another from an open position to a closed position in response to insertion of the post of the surgical retractor blade into the socket; and (b) a slot defined between the base portions of the jaws;

a sliding rod sliding within the elongated member having a distal tip sliding into the slot between the base portions of the jaws when the sliding rod is extended toward the socket, to thereby lock the jaws in the closed position around the post of the retractor blade, and wherein the distal tip retracts from the slot when the sliding rod is retracted to allow the jaw to be spring-biased to the open position.

6. The adaptor of claim 5 further comprising a handle connected to and extending from the sliding rod through the elongated member for manual operation of the sliding rod.

7. The adaptor of claim 5 further comprising a spring biasing the sliding rod in an extended position to lock the jaws in the closed position.

8. The adaptor of claim 5 further comprising springs biasing the jaws in the open position when the sliding rod is retracted.

\* \* \* \* \*